United States Patent

Karrer et al.

[11] Patent Number: 4,609,698
[45] Date of Patent: Sep. 2, 1986

[54] OLIGOESTERS CONTAINING POLYALKYLPIPERIDINE GROUPS

[75] Inventors: Friedrich Karrer, Zofingen; Jean Rody, Riehen, both of Switzerland

[73] Assignee: Ciba-Geigy Corporation, Ardsley, N.Y.

[21] Appl. No.: 728,011

[22] Filed: Apr. 26, 1985

Related U.S. Application Data

[63] Continuation of Ser. No. 589,918, Mar. 15, 1984, abandoned.

[30] Foreign Application Priority Data

Mar. 21, 1983 [CH] Switzerland .................... 1513/83

[51] Int. Cl.$^4$ .............................................. C08K 5/34
[52] U.S. Cl. ..................................... 524/99; 524/102; 524/103; 544/121; 544/129; 544/364; 546/187; 546/188; 546/189; 546/190; 546/191
[58] Field of Search .................... 524/99, 102, 103; 546/188, 189, 242, 187, 190, 191; 544/121, 129, 364

[56] References Cited

U.S. PATENT DOCUMENTS

| | | | |
|---|---|---|---|
| 4,210,576 | 7/1980 | Battista et al. | 546/190 |
| 4,233,412 | 11/1980 | Rody et al. | 525/167 |
| 4,234,707 | 11/1980 | Rody et al. | 525/437 |
| 4,237,297 | 12/1980 | Rody et al. | 546/189 |
| 4,314,933 | 2/1982 | Berner | 428/416 |
| 4,348,524 | 9/1982 | Karrer et al. | 546/190 |

*Primary Examiner*—John Kight
*Assistant Examiner*—Kriellion Morgar
*Attorney, Agent, or Firm*—Luther A. R. Hall

[57] ABSTRACT

Oligomeric esters of the formula I or II

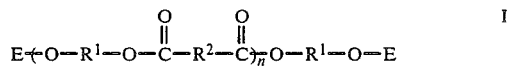

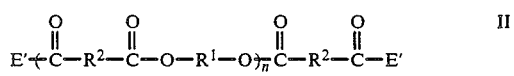

in which n has a value from 1 to 3, $R^1$ and $R^2$ are divalent organic radicals, at least one of which contains a polyalkylpiperidine radical of the formula III

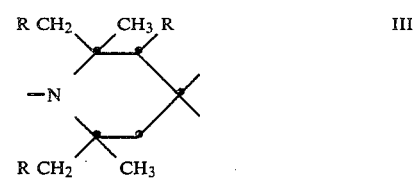

in which R is hydrogen or $C_1$–$C_4$-alkyl and E and E' are end groups, are prepared by polycondensing a dicarboxylic acid ester with a diol, one of the two components being used in a molar excess of 33 to 100%. The end groups of these oligoesters can be modified by reaction with a monofunctional component. If two different dicarboxylic acid esters or diols are used, the corresponding co-oligoesters are obtained. All these oligoesters are valuable light stabilisers for light-sensitive organic material, especially for polymer.

8 Claims, No Drawings

OLIGOESTERS CONTAINING POLYALKYLPIPERIDINE GROUPS

This is a continuation of application Ser. No. 589,918, filed on Mar. 15, 1984, now abandoned.

The invention relates to oligomeric esters formed from dicarboxylic acids and dialcohols and containing at least one polyalkylpiperidine group, and to the use of these compounds as light stabilisers for organic material.

Polyesters containing polyalkylpiperidine groups and having a molecular weight ($\overline{Mn}$) of about 1000 to 5000 have already been described in German Offenlegungsschrift No. 2,719,131 as valuable light stabilisers for plastics. Compared with low-molecular polyalkylpiperidine derivatives, these polymeric light stabilisers have the advantage of lower volatility and extractability. They are prepared by subjecting to polycondensation approximately equimolar amounts of a dicarboxylic acid or dialkyl esters thereof with a diol, at least one of the two components containing a polyalkylpiperidine radical. The end groups of these polyesters are the functional groups of the starting materials, i.e. hydroxyl groups and carboxyl or alkyl carboxylate groups. A general disadvantage of this method of preparation is the poor reproducibility in the molecular weight of the polyesters prepared. In addition, the functional end groups can exercise an interfering action for certain end uses.

As a further development of the inventive idea of providing polymeric light stabilisers, it has therefore been proposed in European Pat. No. A1-2005 and U.S. Pat. No. 4,234,707 to block the end groups by the addition of a monofunctional compound during or after the preparation of the oligomeric polyester, and thus to limit the molecular weight and to obtain products having a reproducible molecular weight. Oligomeric polyesters having a molecular weight ($\overline{Mn}$) of about 2000 to 3000 are thus obtained by adding 5 to 20 mole % of a monocarboxylic acid ester or of a monoalcohol to the polycondensation reaction. The oligomeric polyesters described which are prepared by this process are brittle resins which soften at relatively low temperatures.

It is desirable for certain purposes to have stabilisers which have an even lower molecular weight, but which still possess the advantages of low volatility and extractability. Products of this type are desirable, for example, for more rapid incorporation into the polymers to be stabilised. For certain purposes it is also desirable to have liquid stabilisers, for example for use in lacquers. However, it is no longer possible to prepare such extremely low-molecular polycondensation products in a reproducible manner by the process of preparation described above, using approximately equimolar amounts of dicarboxylic acid and diol.

It has been found that polyesters containing polyalkylpiperidine groups and having an extremely low degree of polycondensation can be prepared in a simple manner by employing, in their preparation by polycondensation from a dicarboxylic acid ester and a diol, one of the two components in a molar excess of 33 to 100%, and, if necessary, subjecting the resulting oligoesters to after-treatment by reaction with an amount of a monofunctional compound corresponding to the end groups.

This process gives products which have the desired combination of properties, of good solubility in the substrate and of low volatility and extractability. These oligoesters have the formula I or II

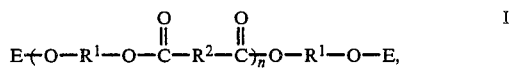

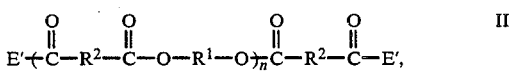

in which n has a value for 1 to 3, $R^1$ and $R^2$ are divalent organic radicals, at least one of which contains a polyalkylpiperidine radical of the formula III

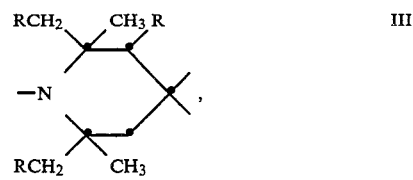

in which R is hydrogen or $C_1$–$C_4$-alkyl, and E and E' are end groups.

As in every polytondensation reaction, the products formed are not single-substance compounds, but mixtures of compounds having different degree of polycondensation. The value n indicated is, therefore, an average value and is not an integer in most cases. However, in the oligoester mixtures formed, a compound having n=1 or 2 or 3 can be present in a predominant amount, if the ratio of the starting components is suitably selected.

If two different diols or the diesters of two different dicarboxylic acids are used as the starting component, co-oligoesters of the formula I or II in which the groups $R^1$ or $R^2$ are different from one another are obtained. These co-oligoesters are also a subject of the invention.

The end groups E in formula I can be hydrogen, in which case the compounds are oligoester-diols. If the latter are subjected to after-treatment with a monofunctional compound, the radical of this monofunctional compound becomes the end group E. The situation concerning the end groups E' is analogous. Without after-treatment, these groups are alkoxy groups, and the products (of the formula II) are oligoester-diesters. If these products are subjected to after-treatment with monofunctional compounds, the radical of the monofunctional compound becomes the end group E'.

The invention relates, in particular, to oligoesters of the formula I or II in which n has a value from 1 to 3, $R^1$ is $C_2$–$C_{18}$-alkylene, $C_4$–$C_8$-alkenylene, $C_4$–$C_{20}$-monooxaalkylene, $C_4$–$C_{20}$-polyoxaalkylene, $C_5$–$C_8$-cycloalkylene, $C_7$–$C_{10}$-cycloalkane-dialkylene, $C_8$–$C_{20}$-arenedialkylene or a divalent radical of the formulae

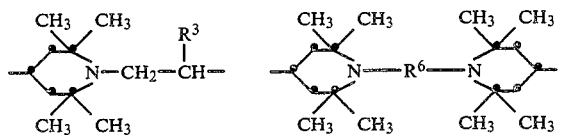
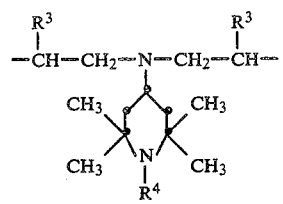
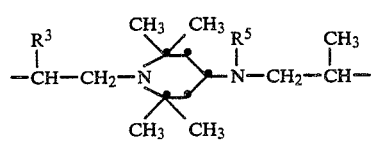
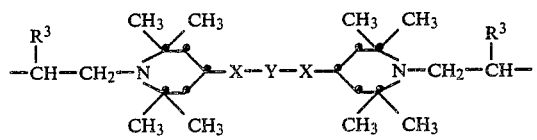
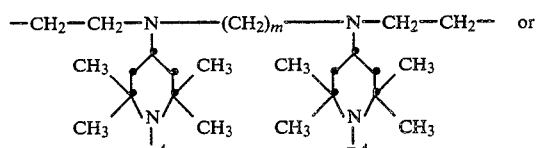
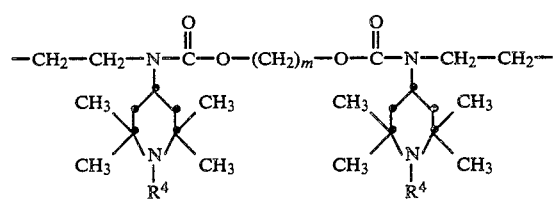
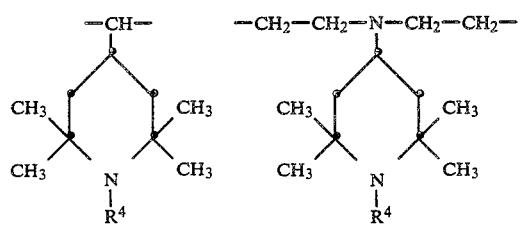

in which m is 2 to 10, X is a group —O— or —NR$^5$—, Y is C$_2$–C$_{12}$-alkylene, C$_4$–C$_{12}$-alkylene which is interrupted by one or two —O— or —NH— groups, cycloalkylene, C$_6$–C$_{12}$-arylene or -phenylene-Z-phenylene- in which Z is —O—, —CH$_2$— or —SO$_2$—, R$^2$ is a direct bond, C$_1$–C$_{18}$-alkylene, C$_2$–C$_6$-alkenylene, C$_5$–C$_8$-cycloalkylene, C$_5$–C$_8$-cycloalkenylene, C$_6$–C$_{12}$-arylene, C$_7$–C$_{12}$-aralkylene or a divalent radical of the formulae

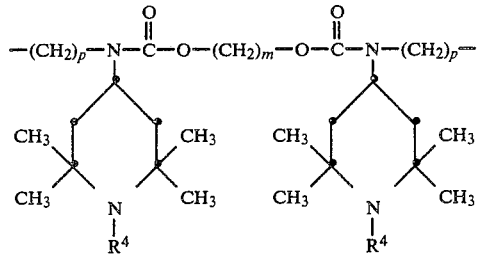

in which p is 1 or 2, E is hydrogen, C$_1$–C$_8$-alkyl, cyclohexyl, benzyl or an acyl group of the formula R$^7$—CO—, R$^8$—O—CO— or (R$^9$)(R$^{10}$)N—CO— and E' is a group R$^{11}$O— or (R$^{12}$)(R$^{13}$)N— and wherein R$^3$ is hydrogen, C$_1$–C$_6$-alkyl, C$_2$–C$_7$-alkoxymethyl, phenoxymethyl or tolyloxymethyl, R$^4$ is hydrogen, C$_1$–C$_8$-alkyl, C$_2$–C$_8$-alkanoyl, C$_3$–C$_6$-alkenoyl, C$_7$–C$_{12}$-phenylalkyl or C$_3$–C$_5$-alkenylmethyl, R$^5$ is hydrogen, C$_1$–C$_{12}$-alkyl, cyclohexyl, phenyl, benzyl, phenylethyl, C$_2$–C$_8$-alkanoyl, C$_3$–C$_6$-alkenoyl or benzoyl, R$^6$ is C$_2$–C$_{12}$-alkylene, C$_4$–C$_8$-alkenylene or xylylene, R$^7$ is C$_1$–C$_{12}$-alkyl, C$_2$–C$_5$-alkenyl, C$_5$–C$_8$-cycloalkyl, C$_6$–C$_{10}$-aryl, C$_7$–C$_{12}$-phenylalkyl or a group of the formula IV $$\text{IV}$$

R$^8$ is C$_1$–C$_{12}$-alkyl, allyl, cyclohexyl or phenyl, R$^9$ is hydrogen, C$_1$–C$_8$-alkyl, allyl, cyclohexyl, phenyl or C$_7$–C$_{10}$-alkylphenyl and R$^{10}$ is C$_1$–C$_8$-alkyl, allyl, cyclohexyl, phenyl or C$_7$–C$_{10}$-alkylphenyl, or R$^9$ and R$_{10}$, together with the N atom to which they are attached, form a 5-membered to 7-membered heterocyclic ring, R$^{11}$ is C$_1$–C$_{12}$-alkyl, C$_3$–C$_5$-alkenylmethyl, C$_5$–C$_8$-cycloalkyl, phenyl, C$_7$–C$_{10}$-alkylphenyl, C$_7$–C$_{12}$-phenylalkyl, C$_3$–C$_{12}$-alkoxyalkyl, a group —(CH$_2$CH$_2$O)$_m$—CH$_3$, a group of the formula IV or a group of the formula V $$\text{V}$$

R$^{12}$ is C$_1$–C$_{12}$-alkyl, allyl, cyclohexyl, phenyl, benzyl, C$_3$–C$_{12}$-alkoxyalkyl, C$_4$–C$_{12}$-dialkylaminoalkyl, a group of the formula IV or a group of the formula VI

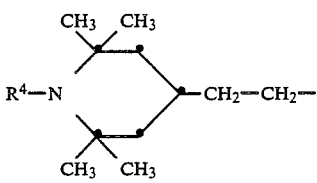

and $R^{13}$ is hydrogen, $C_1$–$C_{12}$-alkyl, allyl, cyclohexyl or a group of the formula IV, and to co-oligomers thereof.

In these compounds, $R^1$ can be linear or branched $C_2$–$C_{18}$-alkylene, for example 1,2-ethylene, 1,3-propylene, 1,2-propylene, tetramethylene, pentamethylene, hexamethylene, octamethylene, decamethylene, dodecamethylene, tetradecamethylene or octadecamethylene, 3-methyl-1,3-butylene, 2,5-hexylene, 2-ethyl-1,3-hexylene, 2,2-dimethyl-1,3-hexylene or 2,2-dimethyl-1,3-propylene.

As $C_4$–$C_8$-alkenylene, $R^1$ can, in particular, be alkenylene-dialkylene, for example 1,4-but-2-enylene, 2,5-hex-3-enylene or 3,6-oct-4-enylene.

As $C_4$–$C_{20}$-monooxaalkylene or $C_4$–$C_{20}$-polyoxaalkylene, $R^1$ can be, for example, 3-oxa-1,5-pentylene, 3,6-dioxa-1,8-octylene, 4-oxa-2,6-heptylene or the divalent radical of a technical polyethylene glycol mixture —(C$H_2$—CH$_2$O)$_r$—CH$_2$—CH$_2$— in which r is 2 to 19, in particular in which r is 2 to 9.

As cycloalkylene or cycloalkane-dialkylene, $R^1$ can be, for example, 1,3-cyclopentylene, 1,3-cyclohexylene, 1,4-cyclohexylene, 1,5-cyclooctylene, cyclohexane-1,3-dimethylene, cyclohexane-1,4-dimethylene or bicyclo[2.2.1]heptane-2,3-dimethylene. As arene-dialkylene, $R^1$ can be, for example, m-xylylene, p-xylylene or biphenyl-4,4'-dimethylene.

As $C_2$–$C_{12}$-alkylene, Y can be linear or branched alkylene, for example dimethylene, trimethylene, tetramethylene, hexamethylene, octamethylene, decamethylene, dodecamethylene, 1,2-propylene or 2,2-dimethyl-1,2-propylene. As alkylene which is interrupted by O or NH, Y can be, for example, 3-aza-1,5-pentylene, 4-aza-1,7-heptylene, 4-oxa-1,7-heptylene, 3,6-diaza-1,8-octylene or 4,11-diaza-1,14-tetradecylene. As $C_6$–$C_{12}$-arylene, Y can be, for example, 1,3-phenylene, 1,4-phenylene, 1,4-naphthylene, 1,5-naphthylene or 4,4'-biphenylene.

As $C_1$–$C_{18}$-alkylene, $R^2$ can be linear or branched alkylene, for example methylene, dimethylene, trimethylene, tetramethylene, hexamethylene, octamethylene or dodecamethylene, 1,2-propylene, 3,3-pentylene, or 2-methyl-1,3-propylene. As $C_2$–$C_6$-alkenylene, $R^2$ can be, for example, vinylene, 1,2-propenylene or 1,3-propenylene.

As cycloalkylene or cycloalkenylene, $R^2$ can be, for example, 1,3-cyclopentylene, 1,4-cyclohexylene, 1,3-cyclohexylene, 1,2-cyclohex-4-enylene or 2,3-bicyclo[2.2.1]hept-5-enylene. As arylene or aralkylene, $R^2$ can be, for example, 1,3-phenylene, 1,4-phenylene, 1,4-naphthylene, 1,5-naphthylene, 4,4'-biphenylene, 1,3-xylylene or 1,4-xylylene.

As $C_2$–$C_{12}$-alkylene, $R^6$ can be, in particular, linear alkylene, for example dimethylene, trimethylene, tetramethylene, hexamethylene or octamethylene. As alkenylene, $R^6$ can be, in particular, 1,4-but-2-enylene.

As $C_1$–$C_6$-alkyl, $R^3$ can be, for example, methyl, ethyl, propyl, n-butyl, sec.-butyl, iso-amyl or n-hexyl. As $C_1$–$C_8$-alkyl, $R^4$, $R^9$, $R^{10}$ and E can additionally also be, for example, n-heptyl, 2-ethylhexyl or n-octyl. As $C_1$–$C_{12}$-alkyl, $R^5$, $R^7$, $R^8$, $R^{11}$, $R^{12}$ and $R^{13}$ can additionally also be, for example, isononyl, n-decyl or n-dodecyl.

As $C_2$–$C_7$-alkoxymethyl, $R^3$ can be, for example, ethoxymethyl, butoxymethyl or 2-ethylbutoxymethyl.

As $C_3$–$C_{12}$-alkoxyalkyl, $R^{11}$ and $R^{12}$ can be, for example, 2-methoxyethyl, 2-isopropoxyethyl, 2-ethoxypropyl, 2-butoxyethyl, 2-(2-ethylhexyloxy)-ethyl, 3-methoxypropyl or 3-ethoxypropyl.

As $C_4$–$C_{12}$-dialkylaminoalkyl, $R^{12}$ can be, in particular, 3-dialkylaminopropyl, for example 3-dimethylaminopropyl or 3-diethylaminopropyl.

As $C_2$–$C_5$-alkenyl, $R^7$ can be, for example, vinyl, prop-2-enyl, 1-prop-2-enyl, 3-prop-1-enyl or 2-methyl-1-prop-1-enyl. As $C_3$–$C_5$-alkenylmethyl, $R^4$ and $R^{11}$ can be, for example, allyl, methallyl or dimethylallyl.

As $C_7$–$C_{12}$-phenylalkyl, $R^4$, $R^7$ and $R^{11}$ can be, for example, benzyl, 2-phenylethyl, 2-phenylpropyl, 2-methyl-2-phenylethyl or 3-phenylpropyl.

As $C_5$–$C_8$-cycloalkyl, $R^7$ and $R^{11}$ can be, for example, cyclopentyl, cyclohexyl or cyclooctyl. As $C_6$–$C_{10}$-aryl, $R^7$ can be phenyl or naphthyl. As $C_7$–$C_{10}$-alkylphenyl, $R^9$, $R^{10}$ and $R^{11}$ can be, for example, tolyl, dimethylphenyl, tert.-butylphenyl or di-(isopropyl)-phenyl.

As $C_2$–$C_8$-alkanoyl, $R^4$ and $R^5$ can be, for example, acetyl, propionyl, butyryl, isobutyroyl, hexanoyl or 2-ethylhexanoyl. As $C_3$–$C_6$-alkenoyl, $R^4$ and $R^5$ can be, for example, acryloyl, methacryloyl or crotonyl.

If $R^9$ and $R^{10}$, together with the N atom to which they are attached, form a 5-membered to 7-membered heterocyclic ring, this can be, for example, a pyrrolidine, piperidine, morpholine, 4-methylpiperazine or 4-(2-cyanoethyl)-piperazine ring.

Preferred oligoesters of the formula I or II are those in which n has a value from 1 to 3, $R^1$ is $C_2$–$C_{12}$-alkylene, $C_4$–$C_{20}$-monooxaalkylene, $C_4$–$C_{20}$-polyoxaalkylene or a group of the formula

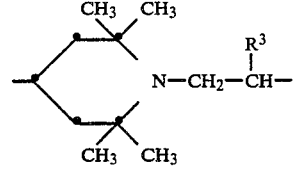

$R^2$ is $C_1$–$C_{12}$-alkylene, $C_2$–$C_{12}$-alkenylene or phenylene, E is hydrogen or a group $R^7$—CO— and E' is a group $R^{11}$O—, $R^3$ is hydrogen, $C_1$–$C_4$-alkyl, $C_2$–$C_6$-alkoxymethyl, phenoxymethyl or tolyloxymethyl, $R^4$ is hydrogen, $C_1$–$C_4$-alkyl, acetyl, allyl or benzyl, $R^7$ is $C_1$–$C_6$-alkyl or phenyl and $R^{11}$ is $C_1$–$C_{12}$-alkyl or a group of the formula IV or V.

The oligoesters can be prepared in solution or without a solvent. Suitable solvents are, in particular, hydrocarbons, such as toluene, xylene, tetralin, decalin or ligroin. The reaction is preferably carried out in the presence of a transesterification catalyst, for example a tetraalkyl titanate, an alkali metal amide, hydride or alkoxide or a dialkyl-tin oxide.

The reaction temperature required for the polycondensation is 80° to 230° C.; the polycondensation is preferably carried out at 120° to 180° C.

The two components can be mixed together at the start or the component used in a less than equivalent quantity is added dropwise in the course of the reaction. The alcohol formed from the ester is distilled off continuously during the reaction in order to displace the equilibrium of the transesterification reaction towards the oligoester. The progress of the reaction can be followed on the basis of the amount of alcohol distilled off. When the calculated amount of the alcohol has been distilled off, the reaction mixture is allowed to cool. The oligoester obtained can be purified by filtration through fuller's earth, silica gel or other adsorptive agents. It can, however, also be used or subsequently reacted with a monofunctional reagent without purification.

If the end groups of the oligoester primarily obtained are hydroxyl groups (formula I, E=H), the monofunctional reagent used can be, for example, an alkyl, cyclohexyl or benzyl halide in the presence of a stoichiometric amount of an alkali (for example in the form of NaH or $C_2H_5ONa$). Ether end groups (E=alkyl, cyclohexyl or benzyl) are thus formed. If the reagent used is a monocarboxylic acid chloride, anhydride or alkyl ester, ester end groups (E=$R^7$CO—) are obtained. If the reagent used is a chlorocarbonate $R^8O$—COCl, carbonate end groups (E=$R^8O$—CO—) are obtained. If a carbamoyl chloride ($R^9$)($R^{10}$)N—CO—Cl is used, carbamate end groups (E=($R^9$)($R^{10}$)N—CO—) are obtained. Other reagents which can react with hydroxyl groups can also be used in a similar manner.

If the end groups of the oligoester are alkoxycarbonyl groups (formula II, E'=—Oalkyl), these groups can be transesterified, for example with a hydroxyl compound $R^{11}OH$, or they are reacted with a primary or secondary amine and amide groups (E'=($R^{12}$)($R^{13}$)N—) are then obtained as end groups.

The reaction with a compound $R^{11}OH$ can also be carried out during the preparation of the oligoester. In this case the compound $R^{11}OH$ can be added either before or during the polycondensation reaction.

The desired oligoesters are obtained in a satisfactorily reproducible molecular weight by the processes indicated here. These products are effective light stabilisers for organic material, for example cosmetics, oils and photographic layers, but particularly for organic polymers such as are used for plastics, lacquers, sealing compounds or adhesives. The following are examples of polymers which can be stabilised in this manner:

1. Polymers of monoolefins and diolefins, for example polyethylene (which can optionally be crosslinked), polypropylene, polyisobutylene, polybut-1-ene, polymethylpent-1-ene, polyisoprene or polybutadiene and polymers of cycloolefins, for example those of cyclopentene or norbornene.

2. Mixtures of the polymers mentioned under 1, for example mixtures of polypropylene and polyisobutylene.

3. Copolymers of monoolefins and diolefins with one another or with other vinyl monomers, for example ethylenepropylene copolymers, propylene-but-1-ene copolymers, propylene-isobutylene copolymers, ethylene-but-1-ene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and salts thereof (ionomers) and also terpolymers of ethylene and propylene and a diene, such as hexadiene, dicyclopentadiene or ethylidenenorbornene.

4. Polystyrene and poly-(p-methylstyrene).

5. Copolymers of styrene or α-methylstyrene with dienes or acrylic derivatives, for example styrene-butadiene, styrene-acrylonitrile, styrene-alkyl methacrylate, styrenemaleic anhydride or styrene-acrylonitrile-methyl acrylate; mixtures of high impact strength formed from styrene copolymers and another polymer, for example a polyacrylate, a diene polymer or an ethylene-propylene-diene terpolymer; and block copolymers of styrene, for example styrene-butadiene-styrene, styrene-isoprene-styrene, styrene-ethylene/butylenestyrene or styrene-ethylene/propylene-styrene.

6. Graft copolymers of styrene, for example styrene on polybutadiene, styrene and acrylonitrile on polybutadiene, styrene and maleic anhydride or polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers and mixtures thereof with the copolymers mentioned under 5, such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers and especially polymers formed from halogen-containing vinyl compounds, for example polyvinyl chloride, polyvinylidene chloride, polyvinyl fluoride and polyvinylidene fluoride; and copolymers thereof, such as vinyl chloride-vinylidene chloride, vinyl chloride-vinyl acetate or vinylidene chloride-vinyl acetate.

8. Polymers derived from α,β-unsaturated acids and derivatives thereof, such as polyacrylates and polymethacrylates, polyacrylamides and polyacrylonitriles.

9. Copolymers of the monomers mentioned under 8 with one another or with other unsaturated monomers, for example acrylonitrile-butadiene copolymers, acrylonitrilealkyl acrylate copolymers, acrylonitrile-alkoxyalkyl acrylate copolymers, acrylonitrile-vinyl halide copolymers or acrylonitrile-alkyl methacrylate-butadiene terpolymers.

10. Polymers derived from unsaturated alcohols and amines or acyl derivatives or acetals thereof, such as polyvinyl alcohol, polyvinyl acetate, stearate, benzoate or maleate, polyvinyl butyral, polyallylphthalate and polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes containing comonomers, for example ethylene oxide.

13. Polyphenyl oxides and sulfides and mixtures thereof with styrene polymers.

14. Polyurethanes derived, on the one hand, from polyethers, polyesters and polybutadienes having terminal hydroxyl groups and, on the other hand, from aliphatic or aromatic polyisocyanates, and also precursors thereof.

15. Polyamides and copolyamides derived from diamines and dicarboxylic acids and/or aminocarboxylic acids or the corresponding lactams, such as polyamide 4, polyamide 6, polyamide 6/6, polyamide 6/10, polyamide 11, polyamide 12, poly-2,4,4-trimethylhexamethylene-terephthalamide, poly-m-phenylene-isophthalamide and block copolymers thereof with polyethers, for example with polyethylene glycol, polypropylene glycol or polytetramethylene glycol.

16. Polyureas, polyimides, polyamide-imides and polybenzimidazoles.

17. Polyesters derived from dicarboxylic acids and dialcohols and/or hydroxycarboxylic acids or the corresponding lactones, such as polyethylene terephthalate, polybutylene terephthalate, poly-1,4-dimethylolcyclohexane terephthalate, polyhydroxybenzoates and block polyether-esters derived from polyethers containing hydroxyl end groups.

18. Polycarbonates.

19. Polysulfones, polyether-sulfones and polyetherketones.

20. Crosslinked polymers derived, on the one hand, from aldehydes and, on the other hand, from phenols, urea or melamine, such as phenol-formaldehyde resins, urea-formaldehyde resins and melamine-formaldehyde resins.

21. Drying and non-drying alkyd resins.

22. Unsaturated polyester resins derived from copolyesters of saturated and unsaturated dicarboxylic acids with polyhydric alcohols, with vinyl compounds as crosslinking agents, and also halogen-containing modifications thereof of low inflammability.

23. Crosslinkable acrylic resins derived from substituted acrylic acid esters, for example from epoxyacrylates, urethane acrylates or polyester acrylates.

24. Alkyd resins, polyester resins and acrylate resins which have been crosslinked with melamine resins, urea resins, polyisocyanates or epoxide resins.

25. Crosslinked epoxide resins derived from polyepoxides, for example from bis-glycidyl ethers or from cycloaliphatic diepoxides.

26. Natural polymers, such as cellulose, natural rubber, gelatine and their polymer-homologously chemically modified derivatives, such as cellulose acetates, propionates and butyrates, and the cellulose ethers, such as methylcellulose.

27. Mixtures (polyblends) of the abovementioned polymers, for example PP/EPDM, polyamide 6/EPDM or ABS, PVC/EVA, PVC/ABS, PVC/MBS, PC/ABS or PBTP/ABS.

The stabilisation of polyolefins, styrene polymers, polyamides, polyurethanes and lacquer resins, such as alkyd, acrylic and polyester resins, is of particular importance.

The oligomeric stabilisers are added to the polymers in a concentration of 0.01 to 5% by weight, calculated on the material to be stabilised. Preferably, 0.1 to 2% by weight of the compounds, calculated on the material to be stabilised, are incorporated into the latter.

The incorporation can be effected during or after polymerisation, for example by mixing the compounds, and, if appropriate, further additives, into the melt by the methods customary in the art, before or during shaping, or by applying the dissolved or dispersed compounds to the polymer, if appropriate with subsequent evaporation of the solvent.

The oligoesters can also be added to the polymers to be stabilised in the form of a masterbatch containing these compounds in a concentration of, for example, 2.5 to 25% by weight.

The invention also relates, therefore, to the polymers which have been stabilised by adding 0.01 to 5% by weight of a compound of the formula I or II, and which can, if necessary, also contain other known and customary additives. The plastics thus stabilised can be used in a very wide variety of forms, for example as films, fibres, tapes, sections or binders for lacquers, adhesives or cements.

The following may be mentioned as examples of further additives together with which the stabilisers which can be used in accordance with the invention can be employed:

1. ANTIOXIDANTS 1.1 Alkylated monophenols, 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert.-butyl-4-methoxymethylphenol.

1.2. Alkylated hydroquinones, 2,6-di-tert.-butyl-4-methoxyphenol, 2,5-di-tert.-butyl-hydroquinone, 2,5-di-tert.-amyl-hydroquinone, 2,6-diphenyl-4-octadecyloxyphenol.

1.3. Hydroxylated thiodiphenyl ethers, 2,2'-thiobis-(6-tert.-butyl-4-methylphenol), 2,2'-thiobis-(4-octylphenol), 4,4'-thiobis-(6-tert.-butyl-3-methylphenol), 4,4'-thiobis(6-tert.-butyl-2-methylphenol)

1.4. Alkylidene-bisphenols, 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.- butylphenol), 2,2'-ethylidene-bis-(4,6-di-tert.-butylphenol), 2,2'-ethylidene-bis-(6-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methylphenyl)-dicyclopentadiene and di-[2-(3'-tert.-butyl-2'-hydroxy-5'-methylbenzyl)-6-tert.-butyl-4-methylphenyl]terephthalate.

1.5. Benzyl compounds, 1,3,5-tri-(3,5-di-tert.-butyl-4-hydroxybenzyl)-2,4,6-trimethylbenzene, di-(3,5-di-tert.-butyl-4-hydroxybenzyl)-sulfide, isooctyl 3,5-di-tert.-butyl-4-hydroxybenzyl mercapto acetate, bis-(4-tert.-butyl-3-hydroxy-2,6-dimethylbenzyl)-dithiol terephthalate, 1,3,5-tris-(3,5-di-tert.-butyl-4-hydroxybenzyl)isocyanurate, 1,3,5-tris-(4-tert.-butyl-3-hydroxy-2,6-dimethylbenzyl)-isocyanurate, dioctadecyl 3,5-di-tert.-butyl-4-hydroxybenzylphosphonate and the calcium salt of monoethyl 3,5-di-tert.-butyl-4-hydroxybenzylphosphonate.

1.6. Acylaminophenols, 4-hydroxylauranilide, 4-hydroxystearanilide, 2,4-bis-octylmercapto-6-(3,5-di-tert.-butyl-4-hydroxyanilino)-s-triazine and octyl N-(3,5-di-tert.-butyl-4-hydroxyphenyl)-carbamate.

1.7. Esters of β-(3,5-di-tert.-butyl-4-hydroxyphenyl-propionic acid with monohydric or polyhydric alcohols, for example with: methanol, octadecanol, 1,6-hexane diol, neopentylglycol, thiodiethylene glycol, diethylene glycol, triethylene glycol, pentaerythritol, tris-hydroxyethyl isocyanurate, di-hydroxyethyl oxaldiamide.

1.8. Esters of β-(5-tert.-butyl-4-hydroxy-3-methylphenyl)-propionic acid with: monohydric or polyhydric alcohols, for example with: methanol, octadecanol, 1,6-hexane diol, neopentylglycol, thiodiethylene glycol, diethylene glycol, triethylene glycol, pentaerythritol, tris-hydroxyethyl isocyanurate, di-hydroxyethyl oxaldiamide.

1.9. Amides of β-(3,5-di-tert.-butyl-4-hydroxyphenyl)-propionic acid, for example: N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine.

2. UV ABSORBERS AND LIGHT STABILISERS 2.1. 2-(2'-Hydroxyphenyl)-benztriazoles, for example the 5'-methyl, 3',5'-di-tert.-butyl, 5'-tert.-butyl, 5'-(1,1,3,3-tetramethylbutyl), 5-chloro-3',5'-di-tert.-butyl, 5-chloro-3'-tert.-butyl-5'-methyl, 3'-sec.-butyl-5'-tert.-butyl, 4'-octoxy, 3',5'-di-tert.-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted or unsubstituted benzoic acids for example 4-tert.-butylphenyl salicylate, phenyl salicylate, octylphenyl salicylate, dibenzoylresorcinol, bis-(4-tert.-butylbenzoyl)-resorcinol, benzoylresorcinol, 2,4-di-tert.-butylphenyl 3,5-di-tert.-butyl-4-hydroxybenzoate and hexadecyl 3,5-di-tert.-butyl-4-hydroxybenzoic acid.

2.4. Acrylates, for example ethyl or isooctyl α-cyano-β,β-diphenylacrylate, methyl α-carbomethoxy cinnamate, methyl or butyl α-cyano-β-methyl-p-methoxy cinnamate, methyl α-carbomethoxy-p-methoxy cinnamate and N-(β-carbomethoxy-β-cyanovinyl)-2-methylindoline.

2.5. Nickel compounds, for example nickel complexes of 2,2'-thiobis-[4-(1,1,3,3-tetramethylbutyl)-phenol], such as the 1:1 or 1:2 complex, if appropriate containing additional ligands, such as n-butylamine, triethanolamine or N-cyclohexyl diethanolamine, nickel dibutyldithiocarbamate, nickel salts of 4-hydroxy-3,5-di-tert.-butylbenzylphosphonic acid monoalkyl esters, such as the methyl or ethyl ester, nickel complexes of ketoximes, such as 2-hydroxy-4-methylphenyl undecyl ketonoxime, and nickel complexes of 1-phenyl-4-lauroyl-5-hydroxypyrazole, if appropriate containing additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert.-butyl-4-hydroxybenzylmalonate, the condensation product formed from 1-hydroxyethyl-2,2,6,6-tetramethyl-4-hydroxypiperidine and succinic acid, the condensation product formed from N,N'-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl) nitrilo triacetate, tetrakis-(2,2,6,6-tetramethyl-4-piperidyl) 1,2,3,4-butanetetracarboxylate and 1,1'-(1,2-ethanediyl)-bis-(3,3,5,5-tetramethyl-piperazinone).

2.7. Oxalic acid diamides, for example 4,4'-di-octyloxyoxanilide, 2,2'-di-octyloxy-5,5'-di-tert.-butyloxanilide, 2,2'-di'-dodecyloxy-5,5'-di-tert.butyl-oxanilide, 2-ethoxy-2'-ethyloxanilide, N,N'-bis-(3-dimethylaminopropyl)-oxalamide, 2-ethoxy-5-tert.-butyl-2'-ethyloxanilide and a mixture thereof with 2-ethoxy-2'-ethyl-5,4'-di-tert.-butyloxanilide and mixtures of ortho-methoxy-substituted and para-methoxy-substituted oxanilides and of o-ethoxy-disubstituted and p-ethoxy-disubstituted oxanilides.

3. Metal deactivators, for example N,N'-diphenyloxaldiamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylideneoxalic acid dihydrazide.

4. Phosphites and phosphonites, for example triphenyl phosphite, diphenylalkyl phosphites, phenyldialkyl phosphites, tri-(nonylphenyl) phosphite, trilauryl phosphite, trioctadecyl phosphite, distearyl pentaerythritol diphosphite, tris-(2,4-di-tert.-butylphenyl) phosphite, diisodecyl pentaerythritol diphosphite, di-(2,4-di-tert.-butylphenyl) pentaerythritol diphosphite, tristearyl sorbityl triphosphite and tetrakis-(2,4-di-tert.-butylphenyl) 4,4'-biphenylenediphosphonite.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilisers, for example copper salts in combination with iodides and/or phosphorus compounds and salts of divalent manganese.

7. Basic co-stabilisers, for example melamine, polyvinylpyrrolidone, dicyanodiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, sodium ricinoleate and K palmitate, and antimony pyrocatecholate or tin pyrocatecholate.

8. Nucleating agents, for example 4-tert.-butylbenzoic acid, adipic acid and diphenyl acetic acid.

9. Fillers and reinforcing agents, for example calcium carbonate, silicates, glass fibres, asbestos, talc, kaolin, mica, barium sulfate, metal oxides and hydroxides, carbon black and graphite.

10. Other additives, for example plasticisers, lubricants, emulsifiers, pigments, fluorescent brighteners, flame-retardants, antistatic agents and blowing agents.

When stabilisers of this type are used concomitantly, synergistic effects can occur, which is frequently the case particularly when UV absorbers are used concomitantly. The oligomers according to the invention can also be used in the form of their salts. Provided that $R^4$ is not an acyl group, the piperidine groups of the oligoesters according to the invention are capable of forming salts with acids, for example with hydrochloric acid, phosphoric acid or sulfonic acids.

The copolymers according to the invention can also be used in the form of their complexes with heavy metal compounds, particularly nickel or cobalt compounds. Examples of these are complexes with nickel acetate, nickel stearate or nickel acetylacetonate.

The examples which follow illustrate the preparation of the oligoesters according to the invention and their use as light stabilisers. The temperatures indicated therein are quoted in degrees C.

EXAMPLE 1

Preparation of an oligoester by polycondensation in a molar ratio of 3:2

1.0 ml of tetrabutyl orthotitanate is added to a solution, heated at 130°–135°, of 172.8 g (0.75 mole) of dimethyl sebacate in 700 ml of anhydrous xylene. 100.7 g (0.50 mole) of 1-hydroxyethyl-4-hydroxy-2,2,6,6-tetramethylpiperidine (HETP) are then introduced continuously into this solution in the course of 4 hours, with stirring. The methanol split off by the progress of the tranesterification—and also some xylene—is removed continuously by distillation in a gentle stream of nitrogen. When the addition of the piperidine is complete, stirring is continued for a further 5 hours at 135°–140°, in the course of which the remainder of the methanol and xylene distil off. The xylene is then removed completely by distillation in vacuo. The residue is taken up in 3:1 hexane/diethyl ether, 25 g of silica gel and 10 g of Tonsil AC are added, and the mixture is stirred for 30 minutes at room temperature. After filtration, the solvents are distilled off and the oligoester is freed from the last traces of solvent in a high vacuum.

The liquid oligoester thus obtained is virtually colourless and has a viscosity of 1970 cP at 40°. The molecular weight ($\overline{Mn}$), determined by vapour pressure osmometry, is 930. This corresponds to an oligoester of the formula

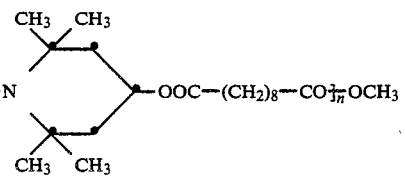

in which n is 1.91.

The oligoesters listed in Table 1 were prepared analogously from the diesters and diols indicated.

TABLE 1

| Oligoester No. | Diester used | Diol* | Molar ratio diester:diol | $\overline{Mn}$ | Physical properties |
|---|---|---|---|---|---|
| 1 | CH$_3$OOC—(CH$_2$)$_8$—COOCH$_3$ | HETP | 3:2 | 800 | Oily liquid |
| 2 | C$_2$H$_5$OOC—(CH$_2$)$_4$—COOC$_2$H$_5$ | HETP | 3:2 | 830 | Oily liquid |
| 3 | C$_2$H$_5$OOC—C(C$_2$H$_5$)$_2$—COOC$_2$H$_5$ | HETP | 3:2 | 944 | Viscous mass |
| 4 | C$_4$H$_9$OOC—(CH$_2$)$_4$—COOC$_4$H$_9$ | HETP | 3:2 | 855 | Oily liquid |
| 5 | CH$_3$OOC—(CH$_2$)$_4$—COOCH$_3$ | HETP | 3:2 | 860 | Oily liquid |

TABLE 1-continued

| Oligoester No. | Diester used | Diol* | Molar ratio diester:diol | $\overline{M}n$ | Physical properties |
|---|---|---|---|---|---|
| 6 | $CH_3OOC-\langle\text{benzene-1,4}\rangle-COOCH_3$ | HETP | 3:2 | 861 | Solid, Ts~55° |
| 7 | $CH_3OOC-(CH_2)_8-COOCH_3$ | HETP | 4:3 | 1240 | Oily liquid |
| 8 | $C_2H_5OOC-C(C_4H_9)_2-COOC_2H_5$ | HPTP | 3:2 | 1030 | Oily liquid |
| 9 | $CH_3OOC-CH(CH_3)-CH_2-C(CH_3)(CH_3)-CH_2-COOCH_3$ | HPTP | 3:2 | 1160 | Oily liquid |
| 10 | $CH_3OOC-(CH_2)_8-COOCH_3$ | HPTP | 3:2 | 910 | Oily liquid |
| 11 | $CH_3OOC-(CH_2)_8-COOCH_3$ | HBTP | 3:2 | 950 | Oily liquid |
| 12 | $CH_3OOC-(CH_2)_8-COOCH_3$ | BHETP | 3:2 | 920 | Oily liquid |
| 13 | $CH_3OOC-\langle\text{benzene-1,3}\rangle-COOCH_3$ | HETP | 3:2 | 1430 | Solid, Ts approx. 180° C. |
| 14 | $CH_3OOC-(CH_2)_7-COOCH_3$ | HETP | 3:2 |  | Oily liquid |
| 15 | $CH_3OOC-CH(CH_3)-CH_2-C(CH_3)(CH_3)-COOCH_3$ | HETP | 3:2 | 980 | Oily liquid |
| 16 | $C_2H_5OOC-C(C_4H_9)_2-COOC_2H_5$ | HETP | 3:2 |  | Oily liquid |

*HETP = 1-(2-Hydroxyethyl)-2,2,6,6-tetramethylpiperidin-4-ol
HPTP = 1-(2-Hydroxypropyl)-2,2,6,6-tetramethylpiperidin-4-ol
HBTP = 1-(2-Hydroxybutyl)-2,2,6,6-tetramethylpiperidin-4-ol
BHETP = 1-(3-Butoxy-2-hydroxypropyl)-2,2,6,6-tetramethylpiperidin-4-ol

EXAMPLE 2

Preparation of a co-oligoester 55.2 g (0.24 mole) of dimethyl sebacate, 10.4 g (0.06 mole) of dimethyl adipate, 40.3 g (0.20 mole) of HETP and 0.5 ml of tetrabutyl titanate are dissolved in 600 ml of anhydrous xylene and stirred, under nitrogen, for 8 hours at 135°–140°, while the methanol formed and part of the xylene are removed by distillation. The remaining xylene is then removed by vacuum distillation, and the oily residue is dissolved in methylene chloride, the solution is filtered through silica gel and the filtrate is evaporated. The last traces of solvent are removed in a high vacuum. The oligoester which remains is an oily, nearly colourless liquid and has a molecular weight ($\overline{M}n$) of 930, determined by vapour pressure osmometry. (Oligoester No. 17).

A co-oligoester is obtained analogously from 0.2 mole of dimethyl sebacate, 0.1 mole of diethyl diethylmalonate and 0.2 mole of HEPT, in the form of a white mass having an $\overline{M}n$ of 1170 (oligoester No. 18).

EXAMPLE 3

Polycondensation followed by reaction of the end groups 0.2 g of lithium amide is added to a solution, heated at 135°, of 32.44 g (0.15 mole) of dimethyl trimethyladipate (mixture of 2,2,4-trimethyl and 2,4,4-trimethyl isomers) in 300 ml of anhydrous xylene. 20.13 g (0.1 mole) of HETP are added to this solution in portions in the course of 4 hours, with stirring. The methanol liberated is removed continuously by distillation in a gentle stream of nitrogen. After a reaction time of a further 6 hours at 135°–140°, free HETP can no longer be detected by chromatography. 19.93 g (0.1 mole) of 1-acetyl-4-hydroxy-2,2,6,6-tetramethylpiperidine, 100 ml of xylene and 0.1 g of lithium amide are then added, and the transesterification is continued for a further 7 hours at 140°, while methanol and xylene are removed by distillation in a stream of nitrogen. After 3 hours at 150° the mixture is cooled, the reaction product is dissolved in hexane, the solution is stirred with 8 g of silica gel for 30 minutes at approx. 20°, and the solvent is removed in vacuo and finally completely removed in a high vacuum.

The oligoester thus obtained has a viscosity of 335 cP at 120°. The average molecular weight, determined by means of the vapour pressure method, is 1150. This corresponds to an oligoester of the formula

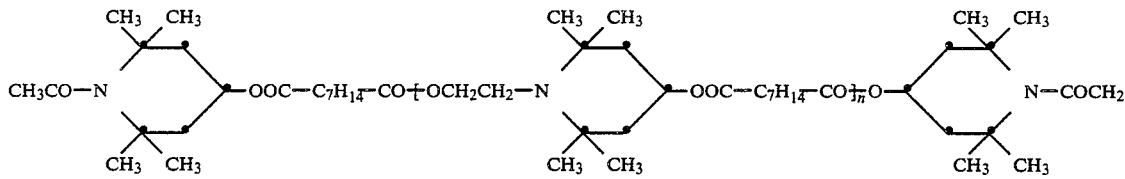

in which n is 1.1.

The oligoesters listed in Table 2 were prepared in an analogous manner for the components indicated.

The samples are subjected to weathering for 2000 hours in an UVCOn accelerated weathering apparatus made by Atlas, using a cycle of 4 hours' irradiation with UV at 60° and 4 hours' weathering at 50°. The 20° gloss as specified in DIN 67,530 is measured after 1000 hours and after 2000 hours. In addition, the samples are investigated for crack formation at regular intervals under a stereomicroscope. The results are listed in Table 3.

TABLE 2

| Oligoester No. | Diester | Diol | Monofunctional component | Molar ratio | $\overline{M}_n$ | Physical properties |
| --- | --- | --- | --- | --- | --- | --- |
| 19 | Dimethyl trimethyladipate | HETP | HO—piperidinyl—N—COCH₃ (2,2,6,6-tetramethyl) | 3:2:2 | 926 | Oily liquid |
| 20 | Diethyl dibutylmalonate | HETP | HO—piperidinyl—N—CH₃ (2,2,6,6-tetramethyl) | 3:2:2 | | Oily liquid |
| 21 | Dimethyl isophthalate | HETP | HO—piperidinyl—N—CH₃ (2,2,6,6-tetramethyl) | 3:2:2 | 750 | Solid, Ts approx. 68° |

EXAMPLE 4

Stabilising a 2-layer metal effect paint

Aluminium sheets 0.5 mm thick are coated with an aluminium-pigmented base coat based on a polyester-/cellulose acetobutyrate/melamine resin. A clear lacquer of the following composition is sprayed onto the wet base coat:

58.3 parts of Viacryl ®VC 373 (acrylic resin made by Vianova, Vienna), 27.3 parts of Maprenal ®MF 590 (melamine resin made by Hoechst AG, Frankfurt), 1.0 part of a 1% solution of a silicone resin in xylene, 4.0 parts of Solvesso ®150 (a mixture of aromatic solvents), 5.4 parts of xylene, 4.0 parts of ethylglycol acetate, 0.5 part of a light stabiliser according to Table 3.

The amount of light stabiliser corresponds to 1% relative to the solids content of the lacquer. This clear lacquer has a viscosity of 21 seconds/DIN Cup 4. It is applied in a layer thickness of 40 μm and is baked for 30 minutes at 130° C.

| Light stabiliser | 20° gloss after 0 | 1000 | 2000 hrs. | Crack formation noticeable after |
| --- | --- | --- | --- | --- |
| None | 97 | 47 | 9 | 1600 hrs. |
| 1% of oligoester No. 1 | 96 | 65 | 35 | 2600 hrs. |
| 1% of oligoester No. 2 | 96 | 56 | 37 | 2800 hrs. |
| 1% of oligoester No. 10 | 95 | 75 | 29 | 2600 hrs. |
| 1% of oligoester No. 18 | 95 | 61 | 40 | 2600 hrs. |

EXAMPLE 5

Stabilising a polypropylene film 100 parts of polypropylene powder (Moplen ®, fibre grade, made by Montedison) are homogenised together with 0.2 part of octadecyl β-(3,5-di-tert.-butyl-4-hydroxyphenyl)-propionate, 0.1 part of calcium stearate and 0.25 part of a stabiliser from Table 1 below in a Brabender plastograph at 200° for 10 minutes. The composition thus obtained is taken as quickly as possible from the kneader and compressed to form a sheet 2–3 mm thick in a toggle plate press. A part of the resulting blank is cut out and compressed between two high-gloss hard aluminium foils by means of a hydraulic laboratory press for 6 minutes at 260° to form a film 0.1 mm thick, which is immediately chilled in cold water. Sections are then punched out of the latter and exposed to illumination in a Xenotest 1200. These specimens are taken out of the exposure apparatus at regular intervals of time and their carbonyl content is tested in an IR spectrophotometer. The increase in the carbonyl extinction at 5.85 μm during exposure is a measure of the photooxidative degradation of the polymer (cf. L. Balaban et al., J. Polymer Sci., Part C; 22 (1969), 1059–1071) and is, according to the invention, associated with a deterioration in the mechanical properties of the polymer. The time taken to reach a carbonyl extinction of 0.25, at which the comparison film is brittle, is taken as a measure of the protective action.

The volatility and ease of extraction with water were checked by (a) heating some of the samples at 120° for 7 days in circulating air oven before exposure, and (b) by treating another fraction of the samples with water at 90° for 7 days before exposure.

Table 4 shows the results without and with pretreatment of the samples.

TABLE 4

| Stabiliser Compound No. | Exposure time (in hours) taken to reach a carbonyl extinction of 0.25 | | |
|---|---|---|---|
| | without pre-treatment | 7 days at 120° | 7 days of extraction with water at 90° |
| 6 | 4230 | 3750 | 2360 |
| 21 | 5300 | 5010 | 1340 |
| None | 1100 | 1070 | 1120 |

What is claimed is:

1. An oligomeric ester of the formula I or II

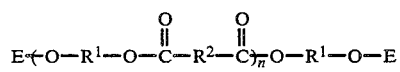

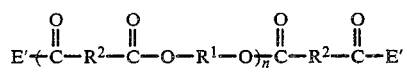

in which n has a value from 1 to 3,

R¹ and R² are divalent organic radicals at least one of which contains a polyalkylpiperidine radical, R¹ is C₂-C₁₈-alkylene, C₄-C₈-alkenylene, C₄-C₂₀-monooxaalkylene, C₄-C₂₀-polyoxaalkylene, C₅-C₈-cycloalkylene, C₇-C₁₀-cycloalkane-dialkylene, C₈-C₂₀-arene-dialkylene or a divalent radical of the formulae

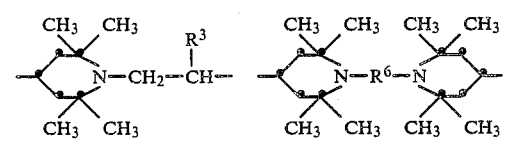

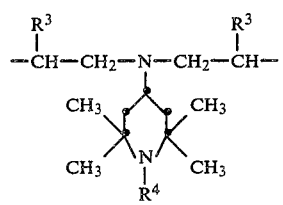

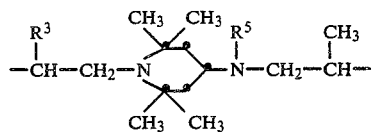

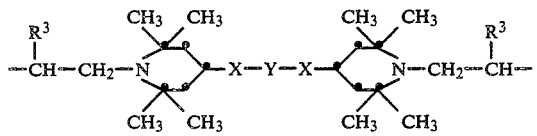

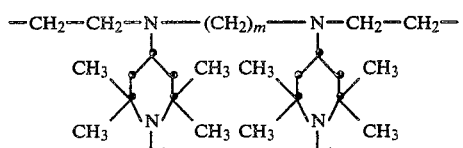

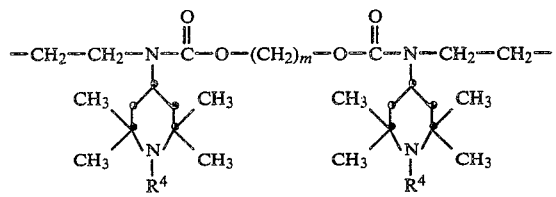

in which m is 2 to 10, X is a group —O— or —NR⁵—, Y is C₂-C₁₂-alkylene, C₄-C₁₂-alkylene which is interrupted by one or two —O— or —NH— groups, cyclohexylene, cyclohexane dimethylene, C₆-C₁₂-arylene or -phenylene-Z-phenylene- in which Z is —O—, —CH₂—, or —SO₂—, R² is a direct bond, C₁-C₁₈-alkylene, C₂-C₆-alkenylene, C₅-C₈-cycloalkylene, C₅-C₈-cycloalkenylene, C₆-C₁₂-arylene, C₇-C₁₂-aralkylene or a divalent radical of the formulae

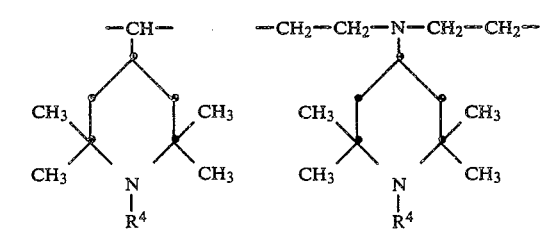

or

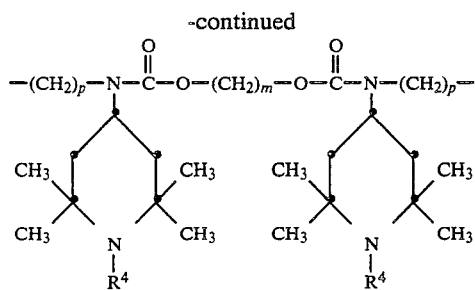

in which p is 1 or 2, E is hydrogen, $C_1$–$C_8$-alkyl, cyclohexyl, benzyl or an acyl group of the formula $R^7$—CO—, $R^8$—O—CO— or $(R^9)(R^{10})N$—CO— and E' is a group $R^{11}O$— or $(R^{12})(R^{13})N$— and wherein $R^3$ is hydrogen, $C_1$–$C_6$-alkyl, $C_2$–$C_7$-alkoxymethyl, phenoxymethyl or tolyloxymethyl, $R^4$ is hydrogen, $C_1$–$C_8$-alkyl, $C_2$–$C_8$-alkanoyl, $C_3$–$C_6$-alkenoyl, $C_7$–$C_{12}$-phenylalkyl or $C_3$–$C_5$-alkenylmethyl, $R^5$ is hydrogen, $C_1$–$C_{12}$-alkyl, cyclohexyl, phenyl, benzyl, phenylethyl, $C_2$–$C_8$-alkanoyl, $C_3$–$C_6$-alkenoyl or benzoyl, $R^6$ is $C_2$–$C_{12}$-alkylene, $C_4$–$C_8$-alkenylene or xylylene, $R^7$ is $C_1$–$C_{12}$-alkyl, $C_2$–$C_5$-alkenyl, $C_5$–$C_8$-cycloalkyl, $C_6$–$C_{10}$-aryl, $C_7$–$C_{12}$-phenylalkyl or a group of the formula

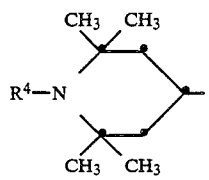    IV $R^8$ is $C_1$–$C_{12}$-alkyl, allyl, cyclohexyl or phenyl, $R^9$ is hydrogen, $C_1$–$C_8$-alkyl, allyl, cyclohexyl, phenyl or $C_7$–$C_{10}$-alkylphenyl and $R^{10}$ is $C_1$–$C_8$-alkyl, allyl, cyclohexyl, phenyl or $C_7$–$C_{10}$-alkylphenyl, or $R^9$ and $R^{10}$, together with the N atom to which they are attached, form a pyrrolidine, piperidine, morpholine, 4-methylpiperazine or 4-(2-cyanoethyl)piperazine ring, $R^{11}$ is $C_1$–$C_{12}$-alkyl, $C_3$–$C_5$-alkenylmethyl, $C_5$–$C_8$-cycloalkyl, phenyl, $C_7$–$C_{10}$-alkylphenyl, $C_7$–$C_{12}$-phenylalkyl, $C_3$–$C_{12}$-alkoxyalkyl, a group —($CH_2CH_2O$)$_m$—$CH_3$, a group of the formula IV or a group of the formula V

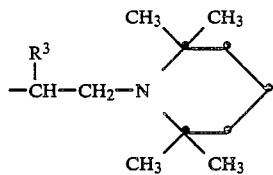    V $R^{12}$ is $C_1$–$C_{12}$-alkyl, allyl, cyclohexyl, phenyl, benzyl, $C_3$–$C_{12}$-alkoxyalkyl, $C_4$–$C_{12}$-dialkylaminoalkyl, a group of the formula IV or a group of the formula VI

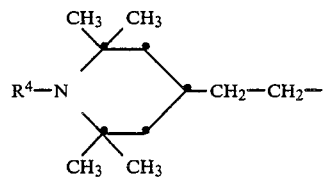    VI and $R^{13}$ is hydrogen, $C_1$–$C_{12}$-alkyl, allyl, cyclohexyl or a group of the formula IV, and to co-oligomers thereof, said oligomeric ester being formed by the polycondensation of a dicarboxylic acid ester and a diol, one of which components being in a molar excess of 33 to 100% of the other.

2. An oligomer as claimed in claim 1 of the formula I or II in which n has a value from 1 to 3, $R^1$ is a group of the formula

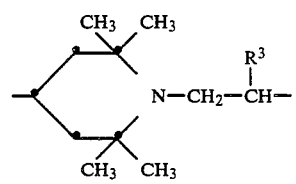

$R^2$ is $C_1$–$C_{12}$-alkylene, $C_2$–$C_{12}$-alkenylene or phenylene, E is hydrogen or a group $R^7$—CO— and E' is a group $R^{11}$—O—, $R^3$ is hydrogen, $C_1$–$C_4$-alkyl, $C_2$–$C_6$-alkoxymethyl, phenoxymethyl or tolyloxymethyl, $R^4$ is hydrogen, $C_1$–$C_4$-alkyl, acetyl, allyl or benzyl, $R^7$ is $C_1$–$C_6$-alkyl or phenyl and $R^{11}$ is $C_1$–$C_{12}$-alkyl or a group of the formula IV or V.

3. An oligoester as claimed in claim 1, which is obtained by reacting dimethyl sebacate with 1-(2-hydroxyethyl)-4-hydroxy-2,2,6,6-tetramethylpiperidine or with 1-(2-hydroxypropyl)-4-hydroxy-2,2,6,6-tetramethylpiperidine in a molar ratio of 3:2.

4. An oligoester as claimed in claim 1, which is obtained by reacting diethyl adipate with 1-(2-hydroxyethyl)-4-hydroxy-2,2,6,6-tetramethylpiperidine in a molar ratio of 3:2.

5. An oligoester as claimed in claim 1, which is obtained by reacting dimethyl isophthalate with 1-(2-hydroxyethyl)-4-hydroxy-2,2,6,6-tetramethylpiperidine in a molar ratio of 3:2.

6. An oligoester as claimed in claim 1, which is obtained by reacting dimethyl 2,2,4-trimethylglutarate with 1-(2-hydroxyethyl)-4-hydroxy-2,2,6,6-tetramethylpiperidine in a molar ratio of 3:2.

7. A method of stabilizing organic material against damage caused by light and UV radiation, by adding an effective amount of at least one compound of the formula I or II of claim 10.

8. A method as claimed in claim 7 of stabilizing organic polymers.

* * * * *